United States Patent
Andrews

(10) Patent No.: US 7,153,321 B2
(45) Date of Patent: Dec. 26, 2006

(54) SURGICAL FORCEPS

(76) Inventor: Emmet Joseph Howard Peter Andrews, 44 Heatherville, Glanimire, Cork (IE)

( * ) Notice: Subject to any disclaimer, the term of this patent is extended or adjusted under 35 U.S.C. 154(b) by 411 days.

(21) Appl. No.: 09/985,863

(22) Filed: Nov. 6, 2001

(65) Prior Publication Data

US 2002/0058965 A1 May 16, 2002

Related U.S. Application Data

(63) Continuation of application No. PCT/IE00/00052, filed on May 8, 2000.

(30) Foreign Application Priority Data

May 7, 1999 (IE) .................................. S990374

(51) Int. Cl.
*A61B 17/28* (2006.01)
(52) U.S. Cl. ................. 606/205; 606/108; 606/207; 606/208
(58) Field of Classification Search ............... 600/184, 600/201, 220, 221, 222, 194, 214, 224; 606/191–195, 606/205–208, 210–211, 108; 81/302; 604/514
See application file for complete search history.

(56) References Cited

U.S. PATENT DOCUMENTS

| | | | | |
|---|---|---|---|---|
| 3,019,790 A | * | 2/1962 | Militana | 606/205 |
| 3,921,641 A | | 11/1975 | Hulka | |
| D262,055 S | * | 11/1981 | Luikart, II | D24/143 |
| 4,462,403 A | | 7/1984 | Martin | |
| 4,608,982 A | * | 9/1986 | Pollard | 606/207 |
| 4,791,925 A | | 12/1988 | Mitterer | |
| 5,014,407 A | * | 5/1991 | Boughten et al. | 29/235 |
| 5,065,650 A | * | 11/1991 | Anderson et al. | 81/486 |
| 5,415,664 A | * | 5/1995 | Pinchuk | 623/1.11 |
| 5,456,695 A | * | 10/1995 | Herve Dallemagne | 606/207 |
| 5,522,839 A | * | 6/1996 | Pilling | 606/207 |
| 5,569,300 A | * | 10/1996 | Redmon | 606/207 |
| 5,683,349 A | * | 11/1997 | Makower et al. | 600/214 |
| 5,690,606 A | * | 11/1997 | Slotman | 600/206 |
| 5,826,467 A | * | 10/1998 | Huang | 81/302 |
| 5,855,590 A | * | 1/1999 | Malecki et al. | 606/205 |
| 5,865,075 A | * | 2/1999 | Medved | 81/302 |
| 5,997,474 A | * | 12/1999 | Batchelor | 600/220 |
| 6,436,117 B1 | * | 8/2002 | Waller et al. | 606/171 |

FOREIGN PATENT DOCUMENTS

| | | |
|---|---|---|
| DE | 33 22 741 A1 | 1/1985 |
| GB | 2198647 A | 6/1986 |

* cited by examiner

OTHER PUBLICATIONS

Patent Specification—"Improvements in Surgical Clamping Devices", Oct. 26, 1937, 474,126, No. 4792/37.

*Primary Examiner*—Julian W. Woo
*Assistant Examiner*—Sarah Webb
(74) *Attorney, Agent, or Firm*—Birch, Stewart, Kolasch & Birch, LLP

(57) ABSTRACT

A surgical forceps has blades of arcuate shape and handles which are urged apart by springs on a guide blade which mounts the blades by a pivot joint. The guide blade projects below the blades. Gripping means formed by bifurcated arms on the guide blade will, when moved apart, grip an intercostal drain tube between grippers. The forceps carrying an intercostal drain tube, can be inserted between a patients ribs and the handles are then moved towards each other to splay the blades apart to provide a channel for the insertion of a tube. The guide blade may also be mounted between the blades.

11 Claims, 8 Drawing Sheets

SURGICAL FORCEPS

This application is a continuation of International application No. PCT/IE00/00052 filed on May 8, 2000, which International Application was published by the International Bureau in English on Nov. 16, 2000.

BACKGROUND OF THE INVENTION

Field of the Invention

The present invention relates to a construction of forceps and in particular to a construction of forceps for the insertion of intercostal chest drains and the like devices into patients.

Collapse of the lung is a serious condition and can often arise due to an injury to the chest. The lung collapses under the pressure of air or blood leakage into the space between the lung and the inside of the chest wall. This usually arises in a state of emergency such as following trauma to the chest requiring urgent medical treatment. The treatment is the insertion of a chest drain between the ribs into the chest cavity. The drain is essentially a flexible plastic tube with a hole at the tip and perforations on either side adjacent the tip. Insertion of the drain is a difficult and hazardous job. It can be performed in several ways.

One way of inserting the drain is by means of a trocar which is a metal rod which is mounted within the drain. The rod has a sharp tip and projects out the hole in the top of the drain for about 5 mm. The trocar is used to force the drain into the chest cavity by piercing through the intercostal muscles. This is a dangerous method of inserting the drain as it is possible to overshoot too deeply into the chest cavity and damage other organs such as the heart, or the large arteries or veins of the chest. Due to these potential lethal hazards the use of the trocar is discouraged.

The recommended method of introduction of the drain is by what is commonly known as the "open technique". This involves the use of a surgical forceps which is a general purpose instrument used in surgery for many different tasks. The forceps is used to separate the muscle fibres situated between the ribs to create a channel for the drain. The drain is then passed through the channel without the use of the trocar. Making the channel with the forceps is no easy task nor indeed is the subsequent manipulation of the drain into position.

While this latter open method is much safer than the use of a trocar, it has many difficulties and limitations. The two major problem areas are the creation of the channel and alignment of the drain to it. These stem from the fact that the forceps is not designed for this job. Indeed it is designed for the exact opposite task: that is for gripping rather than separating tissue. As the tips of the forceps are blunt, considerable inward force has to be applied to penetrate the muscle causing some trauma to the area. Since, as mentioned already, the forceps are designed for gripping rather than separating and therefore using them in the reverse mode to separate the muscle does not provide optimum power or manipulation. Indeed, they are extremely awkward to use. Thus, it requires several spreading actions to create an adequate channel through the muscle leading to excess damage and trauma to the muscle.

When the forceps has formed the required channel, it is then necessary to maintain the channel open with the forceps as the drain is inserted through the muscle channel into the chest cavity. This leads to the second major problem with the current methods: alignment of the drain to the channel. The tip of the drain has now to be inserted and aligned with the channel which is effectively occupied mainly by the forceps. It is always difficult to thread the drain through the remaining part of the channel along the forceps. The safest way that this is done is by using a second forceps to grip the drain and force it through. This in turn causes damage to the drain and an even wider channel to be made.

A further problem of removing the forceps and positioning the drain into the correct position is then encountered. When two forceps are used, pulling out either of the forceps in the tight confined space of the muscle channel may inadvertently dislodge the drain. The drain is required to be positioned either upward to drain air or downward to drain blood or fluid as indicated. This task is difficult with the limitations of the ferceps to direct the drain once inside the chest cavity.

In summary, trocars, though reasonably efficient in operation, are dangerous 4 especially in emergencies where medical personnel are under stress or are working in less than ideal conditions. The trocar can be positively lethal. The use of a surgical forceps to insert the chest drain is a safer method of carrying out the procedure but is inefficient and is associated with many difficulties and problems such as those referred to above.

While the discussion above has related specifically to intercostal drains, it should be appreciated that the present invention is directed towards the introduction of not alone intercostal drains, but any other such drains, tubes or devices into body structures included, but not limited to, the abdominal cavity, the oro-pharynx, larynx or pharynx, any part of the intestinal tract, any vascular structure or other anatomical or pathological structure within the human body. However, in this specification, reference is only made generally to intercostal chest drains but it will be appreciated that the term has to be used in the broadest sense.

OBJECT OF THE INVENTION

The present invention is directed towards providing an improved method and apparatus for the insertion of an intercostal chest drain or the like device into the bodies of mammals.

SUMMARY OF THE INVENTION

According to the invention, there is provided a scissors-like surgical forceps comprising:
  a pair of arms;
  a pivot joint connecting the arms intermediate their ends;
  each arm on one side of the pivot joint comprising a blade;
  each arm on the other side of the pivot joint comprising a handle;
  the arms being cranked adjacent the pivot joint whereby the handles are splayed apart with the blades in engagement; and
  a connector for releasably securing a length of tubing mounted on the pivot joint.

Such an implement will facilitate physicians in the execution of numerous medical procedures, most notably in the insertion of intercostal drains. By having the arms cranked adjacent the pivot joint, the physician may insert the blades into the chest cavity before closing the handles together thereby forcing the blades apart. This provides a suitable aperture in the chest wall for insertion of the intercostal drain. By having the arms cranked adjacent the pivot joint, the optimum force may be exerted by the user on the handles to provide a separating action. The handles are in the correct position for allowing the blades to be splayed apart, for example, to make way for the insertion of an intercostal drain. Of course, other lengths of tubing for different procedures may also be carried on the scissors-like instrument. Alternatively, the connector could be mounted on one of the arms of the forceps. This would provide the physician with the benefit of having the tubing ready for insertion.

Ideally, each blade is arcuate in shape and has an open mouth which faces the open mouth of the other blade. These arcuate shaped mouths are such that a channel will be formed by the blades which will guide the tubing when it is being inserted into a patient. Also, by having arcuate shaped blades, less damage is done to the surrounding tissue and muscle during a procedure. The blades are preferably tapered towards their free end which will further aid insertion of the blades and assist in creating a suitably sized aperture.

In another embodiment of the invention, there is provided a third guide blade mounted on the pivot joint. Alternatively, the guide blade may carry the pivot joint. This guide blade may be below or between the other blades and is particularly useful for guiding the forceps during insertion. For example, the guide blade may be placed on top of a rib during a procedure to insert an intercostal drain. This will avoid damage to the blood vessels located just below each rib which is a common problem experienced when carrying out such a delicate operation. It can further act to guide the drain as it is being inserted through the muscle wall into the chest cavity and act as a guide in the chest cavity thereafter.

The guide blade may be substantially flat and tapers towards its free end. It may also carry the pivot pin to form the pivot joint. The guide blade may be substantially rectangular in cross section tapering from the pivot joint to its free end.

In one embodiment of the invention, the guide blade is mounted between the other blades so that it is sandwiched between the other blades with the handles splayed apart.

In a further embodiment of the invention, the guide blade extends rearwardly of the pivot joint and has gripping means to grip a length of tubing. The guide blade may separate into a bifurcated portion rearward of the pivot joint whereby each arm of the bifurcated portion has a gripping means, preferably arcuate in shape, to grip a length of tubing. These arms may be urged apart to form releasable grip means. The arms may cross over each other in the absence of a length of tubing. By crossing the arms over each other, they will be biased together and so will grip the length of tubing.

In a further embodiment of the invention, the blades project approximately the same height above the guide blade as the intercostal drain. This will ensure an easier entry of the drain into a chest cavity.

The handles are preferably spring urged apart and there may be provided a spring in contact with both a handle and the guide blade to urge the two handles apart from each other. This will keep the handles splayed apart when the forceps is at rest.

In one embodiment there is provided a surgical forceps in which the blades may be forced apart by bringing the handles together and in which there is provided gripping means for carrying a length of tubing. There is further provided a surgical forceps having arcuate shaped blades to provide a passageway for a length of tubing to be inserted into a patient once the blades are in the desired position.

There may be additionally provided a surgical forceps in which there is provided a guide blade for suitably positioning the surgical forceps when carrying out a procedure. This guide blade may be provided with means to grip a length of tubing.

BRIEF DESCRIPTION OF THE DRAWINGS

The invention will be more clearly understood from the following description of some embodiments thereof given by way of example only with reference to the accompanying drawings in which.

DETAILED DESCRIPTION OF THE PREFERRED EMBODIMENTS

Figure 1:
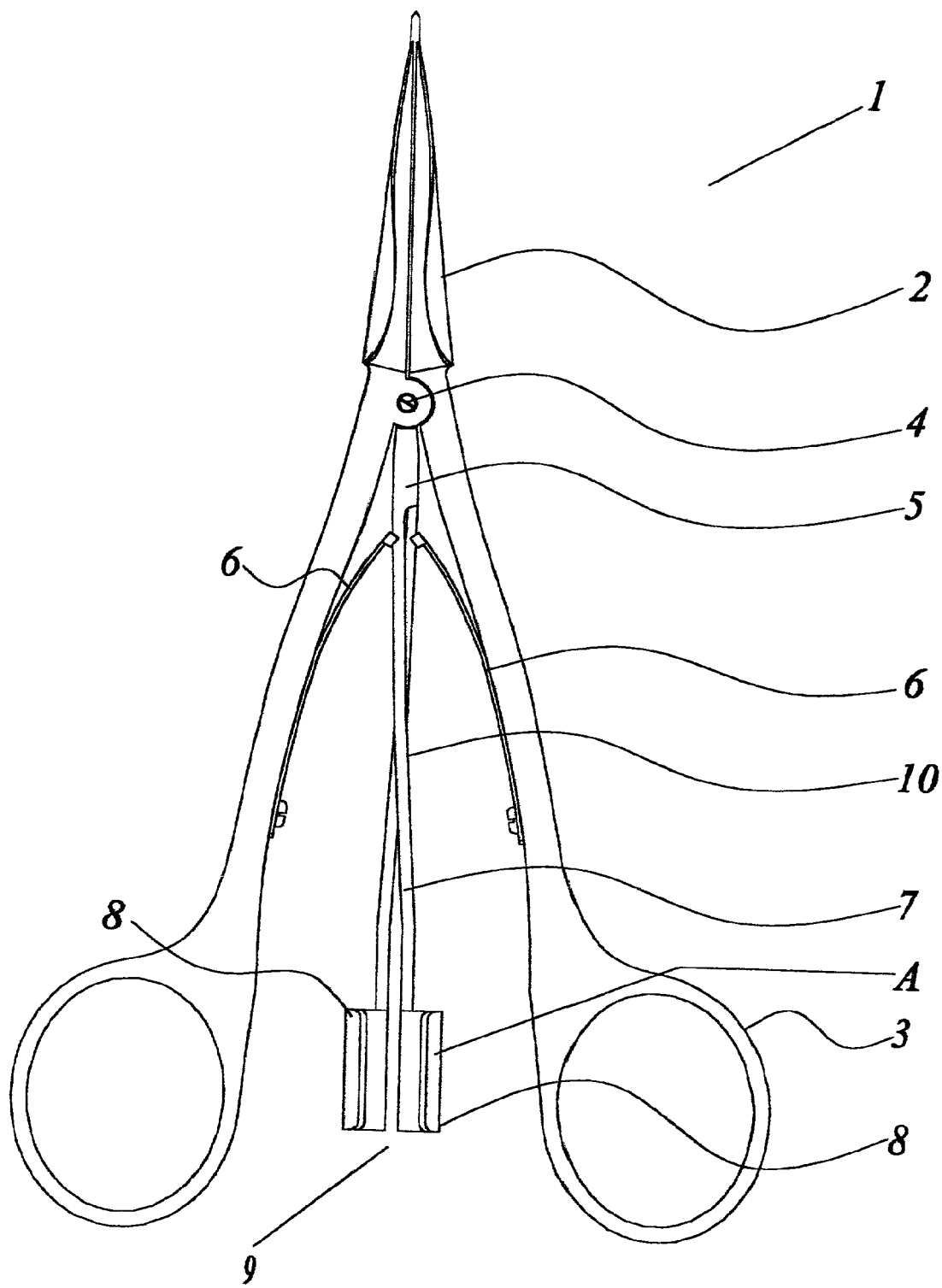
FIG. 1 is a plan view in the closed position of a surgical forceps according to the present invention.
Figure 2:
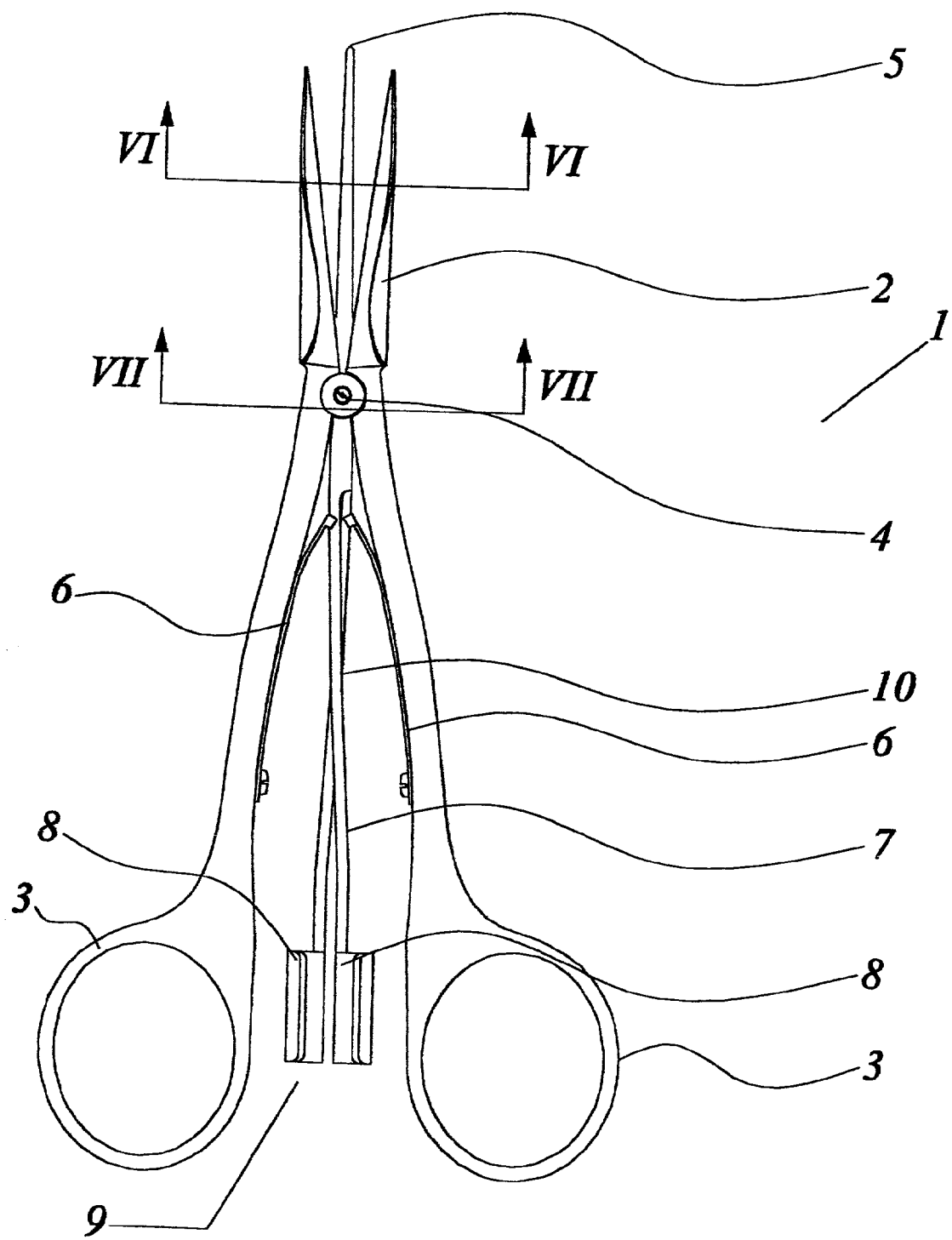
FIG. 2 is a plan view of the forceps in the open position.
Figure 7:
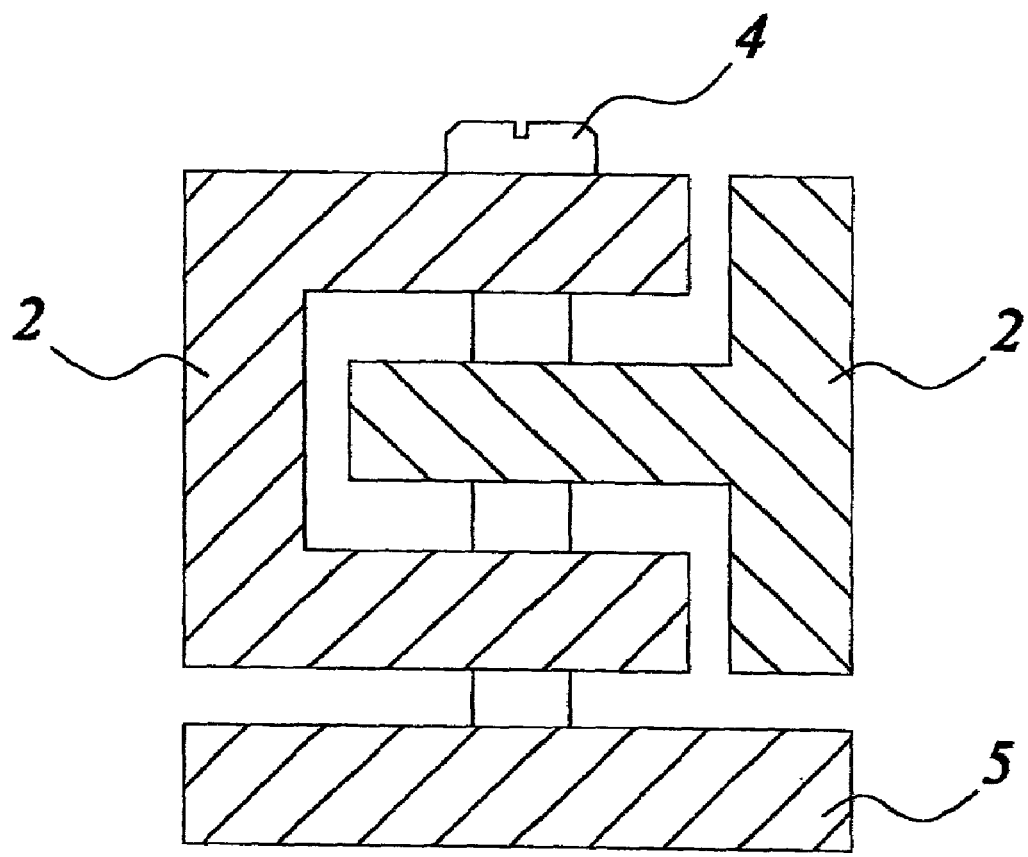
FIG. 7 is an enlarged sectional view along the lines VII—VII of FIG. 2.
Figures 8, 9:
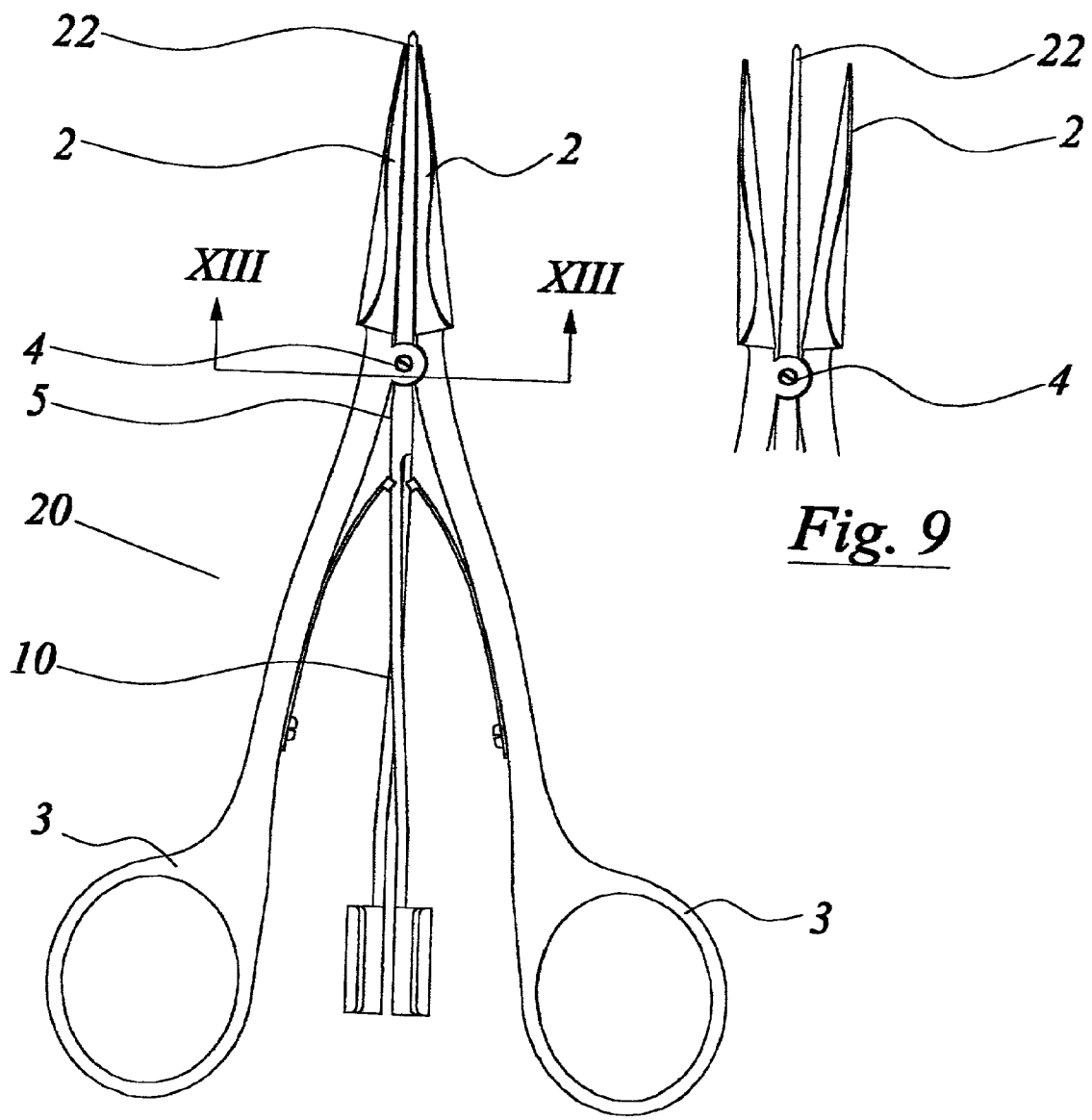
FIG. 8 is a plan view in the closed position of an alternative construction of surgical forceps.
FIG. 9 is a plan view of portion of the surgical forceps of FIG. 8 in the open position.
Figure 10:
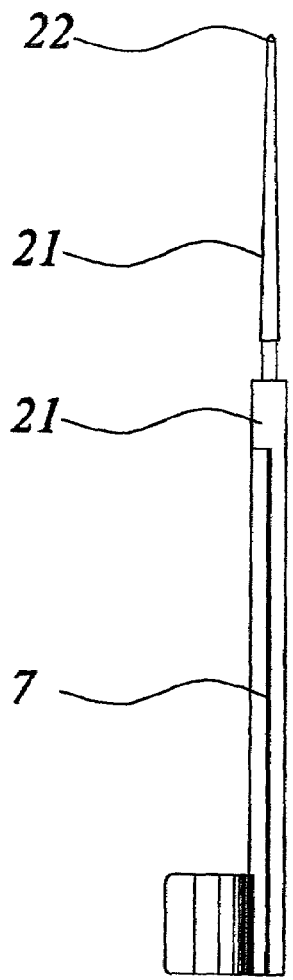
FIG. 10 is a side view of a guide blade forming part of the surgical forceps of FIG. 8.
Figure 11:
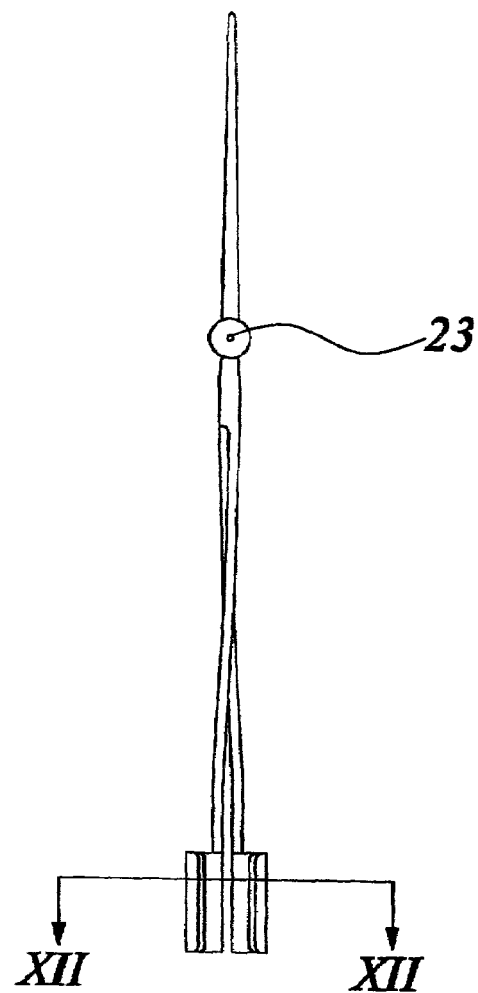
FIG. 11 is a side view of the guide blade.
Figure 12:
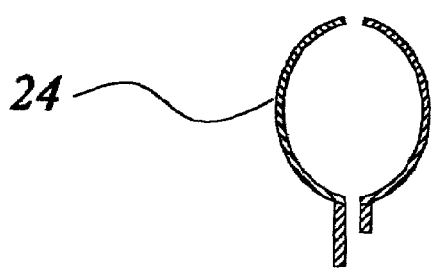
FIG. 12 is a sectional view in the direction of the arrows XII—XII of FIG. 11.
Figure 13:
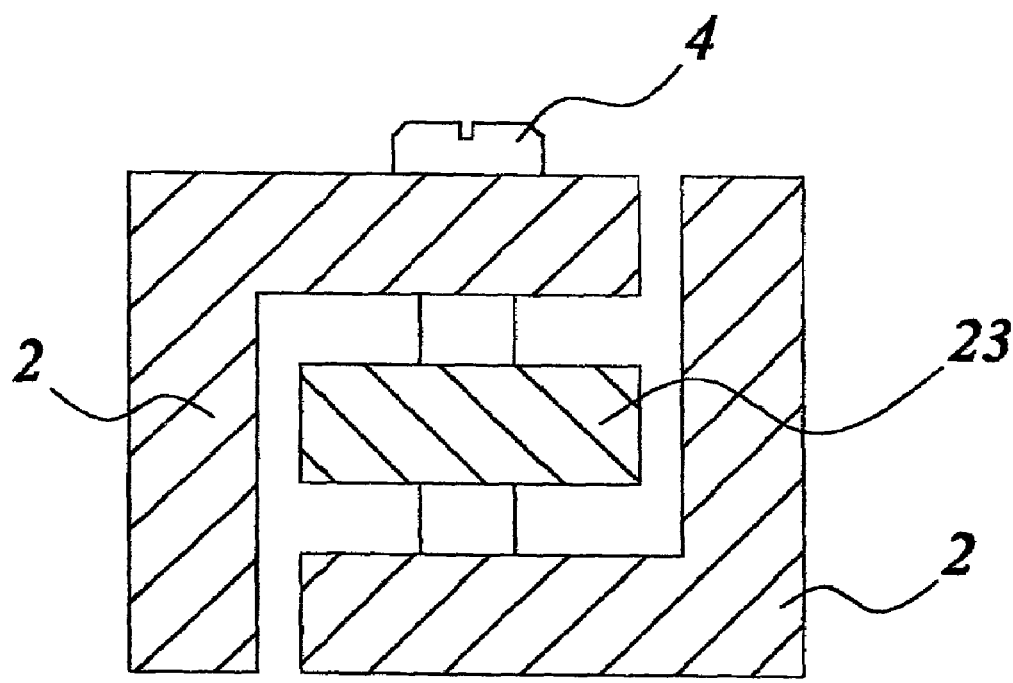
FIG. 13 is an enlarged sectional view along the lines XII–XIII of FIG. 8.

Referring to the drawings there is provided a surgical forceps indicated generally by the reference numeral 1 having a pair of curved blades 2 extending rearwardly to form integral handles 3. The blades 2 are mounted together by a pivot joint 4 provided by a pivot pin on a further guide blade 5. The guide blade 5 carries leaf springs 6 which engage the handles 3 to force the blades into the closed position as can be seen in FIG. 1. It will be noted from FIG. 7 that the guide blade 5 is below the blades 2 and handles 3 at the pivot joint 4. It is possible to refer here to the blades 2 or handles 3 since this is where the transition occurs between each blade 2 and handle 3. For convenience and consistency, reference is made throughout to the blades 2 at the pivot joint 4. The guide blade 5 extends rearwardly to terminate bifurcated arms 7 each carrying an arcuate drain gripper 8 to form releasable grip means to carry an intercostal drain. The releasable grip means is indicated generally by the reference numeral 9. It will be noted that the bifurcated arms 7 cross intermediate their ends at 10.

Figure 3:
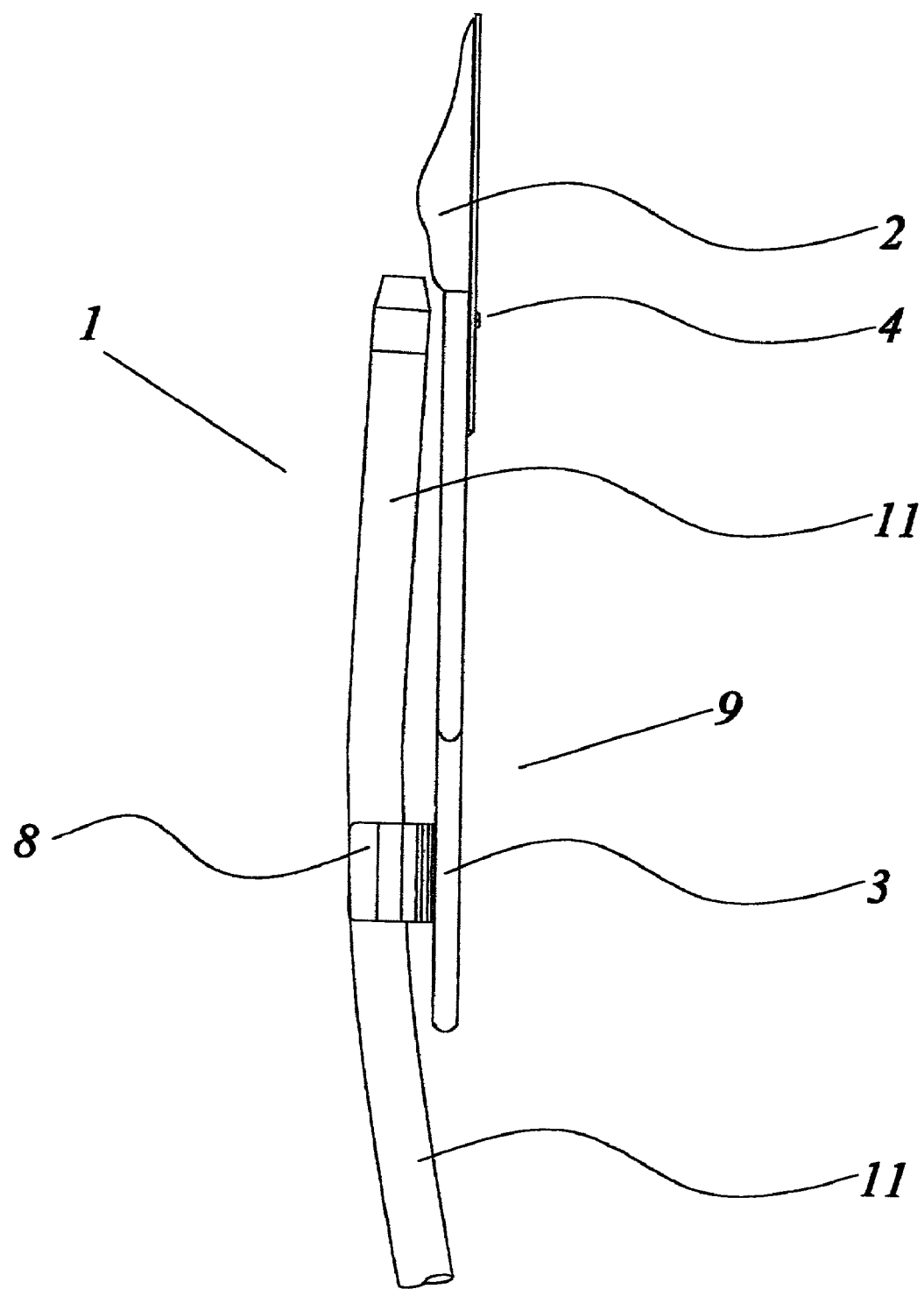
FIG. 3 is a side view of the forceps carrying the chest drain.
Figure 4:
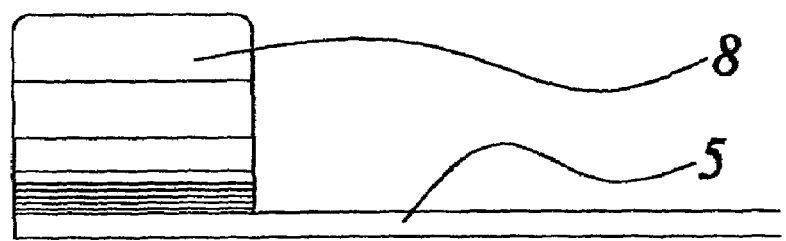
FIG. 4 is a detailed side view of portion of the forceps in the direction of the arrow A of FIG. 1.
Figure 5:
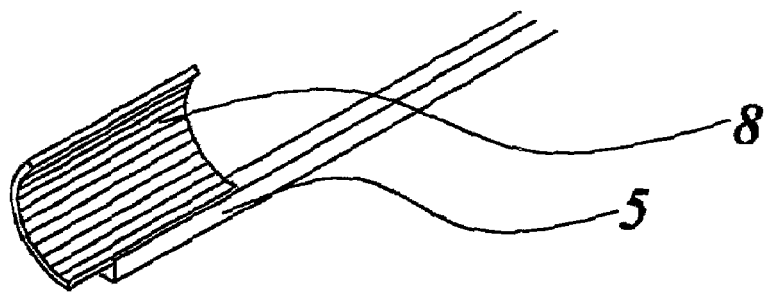
FIG. 5 is a perspective view again in the direction of the arrow A of FIG. 1.
Figure 6:
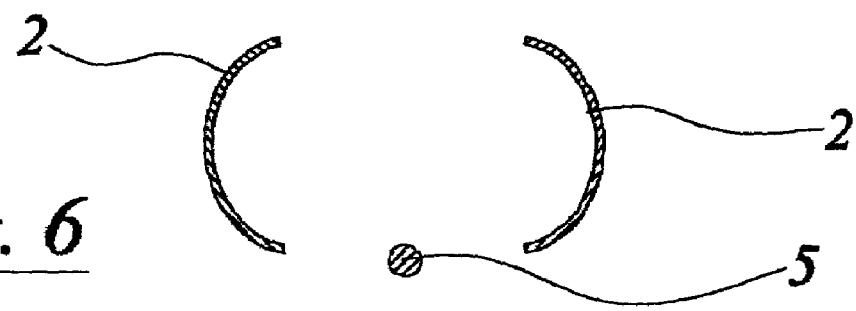
FIG. 6 is a sectional view along the lines VI—VI of FIG. 2.

Referring to FIG. 3 there is illustrated portion of a conventional intercostal chest drain 11 mounted between the arcuate drain grips 8 on the bifurcated arms 7. Because the bifurcated arms 7 cross, the grips 8 exert a gripping action on the intercostal chest drain 11.

In operation it will be appreciated that the drain 11 can be placed at any time, and therefore secured in position, on the arcuate drain grips 8 and the guide blade 3 and blades 2 in the position illustrated in FIG. 1 can be inserted into the intercostal muscle of a patient. The handles 3 can be manipulated to separate the curved blades 2 thus creating the channel through the muscle for the drain. Meanwhile the guide blade 5, which will be held stationary by the leaf springs 6, forms a guide for the forceps. Thus, the forceps can be inserted generally into the chest cavity. Essentially it will be appreciated that the blades 2 provide the separating action to split the muscle and their curvature along the inside of their length creates a hollow center. A circular conduit or channel of the appropriate size is therefore provided for easy passage of the drain 10.

It will be noted that in the embodiment described above, the blades 2 and the releasable grip means 9 are so configured as to carry the intercostal drain 11 directly behind the blades 2. Further, it will be noted that the drain 11 is slightly below or in line with the deepest portion of the blades 2. This ensures that the drain 11 will easily follow in the channel created by the blades 2.

Referring now to FIGS. 8 to 13 inclusive, there is illustrated an alternative construction of surgical forceps, indicated generally by the reference numeral 20, in which parts substantially similar to the parts previously described are identified by the same reference numerals. Minor variations in construction are, where necessary, described below. In this embodiment, there is provided a guide blade 21 substantially rectangular in cross section terminating in a rectangular tip 22. The guide blade 21 extends rearwardly from a central boss 23 to again terminate in bifurcated arms 7 carrying solid arcuate drain grips 24. It will be noted from FIG. 13 that one blade 2 lies above the other blade 2 and on either side of the central boss 23 where they are retained on the guide blade 21 by the pivot joint 4. Further, as can be seen from FIG. 8, the tip 22 of the guide blade 21 projects slightly beyond the other blades 2 which also are of slightly different construction than the previous blades 2.

It will be appreciated that the actual physical configuration and construction of the forceps can be varied depending on its proposed use. For example, the shape of the handles may be chosen as to prevent excessive expansion of the blades at their tips thus reducing damage to a patients muscle.

The advantage of the guide blade is that not alone does it provide a guide for the forceps but it also directs the drain, which is held in alignment along the guide blade by the arcuate drain grips, directly through the channel. Since the drain can be carried on the guide blade as the bore is formed, there is no need to further manipulate or align the drain. When the drain is inserted into the chest cavity then the arcuate drain grips can be easily disengaged to allow the forceps to be disconnected and removed from the muscle channel without disturbing the position of the drain. One of the major advantages of the third blade is that it allows the forceps to be positioned over the apex of the rib so preventing the other blades from damaging blood vessels that are sited just below each rib.

However, one of the most important features of the present invention is that since the handles operate the blades in the same direction they are much easier to manipulate than the conventional forceps. It should be noted that the term "blades in engagement" is used somewhat loosely in the specification in the sense, not alone of actual contact, but as close as they can get having regard to the configuration of the forceps since, in certain constructions, the guide blade may prevent actual contact.

As has been explained already, the surgical forceps could be used to introduce drains or other devices into the abdominal cavity, the oro-pharynx, larynx or pharynx, the intestinal tract, or indeed any vascular structure or other anatomical or pathological structure within the human body. While the invention is particularly used in connection with intercostal drains, it is not to be limited to the use with them.

In the specification the terms "comprise", "comprises", "comprised" and "comprising" or any variation thereof and the terms "include", "includes", "included" and "including" or any variation thereof are considered to be totally interchangeable and they should all be afforded the widest possible interpretation and vice versa.

The invention is not limited to the embodiments hereinbefore described but may be varied in both construction and detail within the scope of the claims.

The invention claimed is:

1. A scissors-like surgical forceps comprising:
   a pair of forcep arms;
   a pivot joint connecting the forcep arms intermediate their ends;
   each forcep arm on one side of the pivot joint comprising a blade;
   each forcep arm on the other side of the pivot joint comprising a handle;
   the forcep arms being cranked adjacent the pivot joint whereby the handles are splayed apart with the blades in engagement; and
   a guide blade mounted on the pivot joint, the guide blade extending rearwardly of the pivot joint and terminating in a bifurcated portion, each bifurcated arm of said bifurcated portion carries a drain gripper of arcuate shape, the bifurcated arms can be urged apart to receive a length of tubing and form releasable grip means.

2. A surgical forceps as claimed in claim 1, in which the bifurcated arms cross intermediate their ends when an intercostal drain is not mounted therein.

3. A surgical forceps as claimed in claim 1, in which the handles are spring urged apart.

4. A surgical forceps as claimed in claim 1, in which a spring is mounted between each handle and the guide blade to urge the handles away from the guide blade and thus apart.

5. A surgical forceps as claimed in claim 1, in which the guide blade lies below the other blades on the pivot joint.

6. A surgical forceps as claimed in claim 1, in which the guide blade lies between the other two blades on the pivot joint.

7. A surgical forceps as claimed in claim 1, in which the guide blade extends forward from the pivot joint substantially the same distance from the pivot joint as the other blades.

8. A surgical forceps as claimed in claim 1, in which the guide blade is substantially flat, tapers towards it free end and carries a pivot pin to form the pivot joint.

9. A scissors-like surgical forceps comprising:
   a pair of forcep arms;
   a pivot joint connecting the forcep arms intermediate their ends;
   each forcep ann on one side of the pivot joint comprising a blade;
   each forcep arm on the other side of the pivot joint comprising a handle;
   the forcep arms being cranked adjacent the pivot joint whereby the handles are splayed apart with the blades in engagement;
   a tube gripping means for releasably securing the exterior of a length of tubing mounted on the pivot joint, whereby the length of tubing is held spaced-apart from and rearwardly of the blades when the blades are being inserted into a patient; and a guide blade mounted on the pivot joint, the guide blade extending substantially the same distance from the pivot joint as the other blades, and the guide blade extending rearwardly of the pivot joint and terminating in a bifurcated portion, each bifurcated arm of said bifurcated portion carries a drain gripper of arcuate shape which can be urged apart to receive the tubing and form the tube gripping means.

10. A surgical forceps as claimed in claim 9, in which the bifurcated arms cross intermediate their ends when an intercostal drain is not mounted therein.

11. A surgical forceps as claimed in claim 9, in which the handles are spring urged apart.

* * * * *